United States Patent
Asada et al.

(10) Patent No.: US 9,677,980 B2
(45) Date of Patent: Jun. 13, 2017

(54) METHOD OF ENTRAPPING CHLORINE DIOXIDE GAS, METHOD OF DETERMINING CONCENTRATION OF CHLORINE DIOXIDE AND ENTRAPPING AGENT FOR CHLORINE DIOXIDE

(71) Applicant: TAIKO PHARMACEUTICAL CO., LTD., Suita-shi, Osaka (JP)

(72) Inventors: Shigeo Asada, Suita (JP); Koichi Nakahara, Suita (JP); Kazuhiko Taguchi, Suita (JP)

(73) Assignee: TAIKO PHARMACEUTICAL CO., LTD., Suita-Shi, Osaka (JP)

( * ) Notice: Subject to any disclaimer, the term of this patent is extended or adjusted under 35 U.S.C. 154(b) by 0 days.

(21) Appl. No.: 14/765,739

(22) PCT Filed: Jan. 21, 2014

(86) PCT No.: PCT/JP2014/051114
§ 371 (c)(1),
(2) Date: Aug. 4, 2015

(87) PCT Pub. No.: WO2014/122983
PCT Pub. Date: Aug. 14, 2014

(65) Prior Publication Data
US 2015/0369713 A1    Dec. 24, 2015

(30) Foreign Application Priority Data

Feb. 5, 2013 (JP) .................................. 2013-020674

(51) Int. Cl.
| | | |
|---|---|---|
| *G01N 1/40* | (2006.01) | |
| *G01N 31/22* | (2006.01) | |
| *B01D 53/14* | (2006.01) | |
| *C01B 11/02* | (2006.01) | |
| *G01N 1/22* | (2006.01) | |

(52) U.S. Cl.
CPC ....... *G01N 1/4044* (2013.01); *B01D 53/1493* (2013.01); *C01B 11/022* (2013.01); *G01N 31/223* (2013.01); *B01D 2252/50* (2013.01); *G01N 1/2202* (2013.01); *G01N 1/2273* (2013.01); *Y10T 436/19* (2015.01)

(58) Field of Classification Search
CPC .......... G01N 1/4044; G01N 1/40; G01N 1/28; G01N 1/00; G01N 31/223; G01N 31/02; G01N 31/16; Y10T 436/19; Y10T 436/00; B01D 53/1493; B01D 53/14; B01D 53/00; B01D 2252/50; B01D 2252/00
USPC ................................ 436/124; 423/240 R, 210
See application file for complete search history.

(56) References Cited

U.S. PATENT DOCUMENTS

| | | | | |
|---|---|---|---|---|
| 5,326,546 | A * | 7/1994 | Rosenblatt ............ | C01B 11/024 252/182.11 |
| 6,663,902 | B1 * | 12/2003 | Hei ........................ | A01N 59/00 422/29 |
| 2005/0005868 | A1 | 1/2005 | Shepard et al. | |
| 2005/0008554 | A1 | 1/2005 | Nowosielski-Slepowron et al. | |
| 2010/0012891 | A1 | 1/2010 | Speronello et al. | |
| 2010/0310418 | A1 | 12/2010 | Mason et al. | |
| 2014/0113007 | A1 * | 4/2014 | Kato ..................... | C01B 11/024 424/665 |

FOREIGN PATENT DOCUMENTS

| | | | |
|---|---|---|---|
| JP | 2007-534455 A | 11/2007 | |
| JP | 2009-122077 A | 6/2009 | |
| JP | 2010-077004 A | 4/2010 | |
| JP | WO 2012/165466 A1 | 12/2012 | |
| WO | WO2012/165466 A1 * | 12/2012 | ............. C01B 11/02 |

OTHER PUBLICATIONS

Stryker, Margaret, Determination of Chlorine and Chlorine Dioxide in Pulp Mill Bleach Plant Vents, National Council of the Paper Industry for Air and Stream Improvement, Inc. Southern Regional Center, 1997, pp. 1-7.*
International Search Report (Form PCT/ISA/210) issued on Apr. 22, 2014, by the Japanese Patent Office in corresponding International Patent Application No. PCT/JP2014/051114. (2 pages).
International Preliminary Report on Patentability (Form PCT/IB/373) and the Written Opinion of the International Searching Authority (Form PCT/ISA/237) issued on Aug. 11, 2015, by the International Bureau of WIPO in corresponding International Application No. PCT/JP2014/051114. (8 pages).
Communication dated Sep. 30, 2016 issued in the corresponding European Patent Application No. 14749434.8-1553 (9 pages).

* cited by examiner

*Primary Examiner* — Christine T Mui
(74) *Attorney, Agent, or Firm* — Buchanan Ingersoll & Rooney PC

(57) ABSTRACT

A method of entrapping chlorine dioxide gas, including the steps of using an aqueous solution containing an alkaline substance and an iodide and bringing air containing the chlorine dioxide gas into contact with the aqueous solution.

10 Claims, No Drawings

METHOD OF ENTRAPPING CHLORINE DIOXIDE GAS, METHOD OF DETERMINING CONCENTRATION OF CHLORINE DIOXIDE AND ENTRAPPING AGENT FOR CHLORINE DIOXIDE

TECHNICAL FIELD

This disclosure relates to an entrapping method, a concentration determining method and an entrapping agent for chlorine dioxide gas contained in a low concentration in air.

BACKGROUND ART

Chlorine dioxide gas is a powerful oxidizer, which is used e.g. in an indoor air environment, for decomposing odorous component for deodorization or for removing/sterilizing virus, bacteria which may be present afloat in the air to cause air-borne infection.

As some examples of conventional methods for determining chlorine dioxide gas concentration in air, there can be cited a method using an electrolysis type sensor utilizing oxidization-reduction reaction and a gas absorption method using iodine solution (see e.g. Non-Patent Document 1).

PRIOR-ART DOCUMENT

Non-Patent Document

Non-Patent Document 1: 2007 International Chemical Substance Summary Evaluation Document No. 37: Chlorine Dioxide (gas), 3.1 Air Monitoring of Working Environment, page 8, National Institute of Health Sciences, Department of Safety Information.

SUMMARY

Problem to be Solved

As chlorine dioxide gas is an unstable substance and can be easily decomposed, it has been very difficult to employ chlorine dioxide gas as reference gas in a method using an electrolysis type sensor (this will be referred to simply as "sensor method" hereinafter). For this reason, such sensor method almost always uses chlorine gas instead of chlorine dioxide gas, as its reference gas. However, when chlorine gas is used as reference gas, the method does not effect the determination directly, thus requiring conversion. And, its conversion factor, due to such influences as pH, etc., varies from 0.5 to 2.5 or the factor varies also according to e.g. a condition used for chlorine gas generation. Thus, the method suffers a problem of being liable to determination error.

On the other hand, in the case of the conventional gas absorption method using iodine solution, as shown by the following chemical formulae (1) and (2), chlorine dioxide gas reacts with iodide contained in the iodine solution, thereby to release iodine, which is then analyzed by iodometric titration method, colorimetric method, etc., which in turn is determined as the concentration of the chlorine dioxide gas.

Reaction between chlorine dioxide and iodide (potassium iodide) under acidic condition:

$$2ClO_2 + 10KI + 8HCl \rightarrow 5I_2 + 10KCl + 4H_2O \quad (1)$$

Reaction between chlorine dioxide and iodide (potassium iodide) under neutral condition:

$$2ClO_2 + 2KI \rightarrow I_2 + 2KClO_2 \quad (2)$$

However, for example, chlorine dioxide gas used in indoor air is often set to a very low concentration. For instance, its concentration is 10 ppb approximately at most, or it even can sometimes be as low as 10 ppb or less.

With the conventional gas absorption method, the method often requires a long period for allowing chlorine dioxide gas at low concentration to be absorbed in the iodine solution. In the course of this process, generated iodine will be stabilized by e.g. potassium iodide. Under the equilibrium condition, however, iodine in a free state is present, which free iodine may be evaporated to escape into the air. This would cause a minus error in the determination.

Moreover, as shown by Chemical Formula (3) below, ozone ($O_3$) present in the air can react with the iodine (e.g. potassium iodide) to generate iodine inadvertently. So, this presence of ozone would cause a plus determination error. Incidentally, it is said that ozone ($O_3$) is present normally at a concentration ranging from about 10 ppb to 30 ppb in the atmosphere.

$$O_3 + 2KI + H_2O \rightarrow I_2 + 2KOH + O_2 \quad (3)$$

The object of the present disclosure is to enable accurate determination of concentration of chlorine dioxide gas contained in a low concentration in air and to make it available for e.g. calibration of an instrument for continuous determination of chlorine dioxide gas concentration with high sensitivity.

Solution

A first characterizing feature of a chlorine dioxide gas entrapping method according to this disclosure lies in that the method comprises the steps of using an aqueous solution containing an alkaline substance and an iodide and bringing air containing the chlorine dioxide gas into contact with the aqueous solution.

[Function and Effect]

The aqueous solution employed in the above-described configuration contains an alkaline substance, thus exhibiting alkaline property.

When chlorine dioxide gas is absorbed in the alkaline aqueous solution containing iodide, as shown by Chemical Formulae (4) through (6) below, there occurs a reaction between chlorine dioxide gas and iodide, which reaction produces a stable iodate and/or iodite (present as very stable iodate ions and/or iodite ions in the alkaline aqueous solution).

$$2ClO_2 + 2KI + 2KOH \rightarrow KIO_2 + KIO_3 + 2KCl + H_2O \quad (4)$$

$$6ClO_2 + 5KI + 6KOH \rightarrow 5KIO_3 + 6KCl + 3H_2O \quad (5)$$

$$4ClO_2 + 5KI + 4KOH \rightarrow 5KIO_2 + 4KCl + 2H_2O \quad (6)$$

Namely, according to the above configuration, although iodine is produced transiently, this iodine will be converted into stable iodate and/or iodite immediately. Therefore, even when air containing chlorine dioxide gas in a low concentration is kept in contact with aqueous solution of a long period, there is no risk of evaporation loss of iodine.

Further, also even in case ozone ($O_3$) present in the air is absorbed in the aqueous solution, as this ozone is decomposed by the alkaline substance contained in the aqueous solution, production of iodine through the reaction between ozone and the iodide can be prevented substantially completely for ozone which is normally present in the atmosphere in a concentration ranging from 10 ppb to 30 ppb approximately.

For the reasons described above, when the chlorine dioxide gas entrapping method proposed by this disclosure is employed, it is possible to prevent not only the determination error attributable to evaporation of iodine, but the determination error attributable to ozone, so air containing chlorine gas in a low concentration can be determined in an accurate manner.

A second characterizing feature lies in that chlorine dioxide gas contained in the air is present in a concentration ranging from 0.0002 ppm to 5 ppm.

[Function and Effect]

With the above-described configuration, as chlorine dioxide gas is ionized before its absorptive entrapment, no diffusion of iodine into the air will occur even when the absorption is effected for a long period. Therefore, chlorine dioxide gas which is contained in the air in a very low concentration ranging from 0.0002 ppm to 5 ppm can be determined in an accurate manner.

A third characterizing feature lies in that the alkaline substance contained in the aqueous solution has a concentration of 0.01 N or more.

[Function and Effect]

If the concentration of the alkaline substance contained in the aqueous solution is below 0.01N, this will promote the reaction between absorbed chlorine dioxide gas and iodide, thus tending to invite release of iodine and also will lead to prolongation of the period for the ionization (above-described production of stable iodate and/or iodite through the reaction between chlorine dioxide gas and iodide), so that there arises risk of increased determination error. On the other hand, if the alkaline substance concentration is 0.01N or more, most of absorbed chlorine dioxide gas will react immediately with iodide, thus being ionized. So that, occurrence of determination error can be prevented in a more reliable manner.

A fourth characterizing feature lies in that the iodide contained in the aqueous solution has a concentration of 0.2 g/L or more.

[Function and Effect]

When the concentration of the iodide contained in the aqueous solution is set to 0.2 g/L or more, the absorbed chlorine dioxide gas will react with the iodide even more reliably. As a result, occurrence of determination error can be prevented in an even more reliable manner.

A characterizing feature of a chlorine dioxide gas concentration determining method according to this disclosure lies in that the method implements the chlorine dioxide gas entrapping method according to any one of the first through fourth characterizing features, the concentration determining method comprises a step of determining, with using an ion chromatography technique, the concentration of iodate and/or iodite in the aqueous solution contacted with the air containing the chlorine dioxide gas.

[Function and Effect]

With the above-described configuration, since the concentration of iodate and/or iodite in the aqueous solution can be determined directly by means of concentration of the solution by the ion chromatography technique. Therefore, the concentration of chlorine dioxide gas contained in a low concentration in the air can be determined in an even more accurate manner.

A further characterizing feature of a chlorine dioxide gas concentration determining method according to this disclosure lies in that the method implements the chlorine dioxide gas entrapping method according to any one of the first through fourth characterizing features, the concentration determining method comprises the steps of making acidic the aqueous solution contacted with the air containing the chlorine dioxide gas so as to release iodine and determining the concentration of the iodine by colorimetric method or iodometric titration method.

[Function and Effect]

With the above-described configuration, by rendering the aqueous solution acidic, as shown by the following Chemical Formulae (7) and (8), iodine can be released immediately from iodate and/or iodite in the aqueous solution. With this, iodine concentration determination is made possible with using the known colorimetric method or iodometric titration method for the aqueous solution. Thus, the concentration of chlorine dioxide gas contained in a low concentration in air can be determined easily.

$$2KIO_2+4H_2SO_4+6KI \rightarrow 4I_2+4K_2SO_4+4H_2O \qquad (7)$$

$$KIO_3+3H_2SO_4+5KI \rightarrow 3I_2+3K_2SO_4+3H_2O \qquad (8)$$

A characterizing feature of a chlorine dioxide gas entrapping agent proposed by the present disclosure lies in that the entrapping agent comprises an aqueous solution containing an alkaline substance and iodide.

[Function and Effect]

The aqueous solution of the above-described configuration contains an alkaline substance, thus exhibiting alkaline property.

When chlorine dioxide gas is absorbed in the alkaline aqueous solution containing iodide, as shown by the Chemical Formulae (4) through (6) above, there occurs a reaction between chlorine dioxide gas and iodide, which reaction produces a stable iodate and/or iodite (present as very stable iodate ions and/or iodite ions in the alkaline aqueous solution).

Namely, with the aqueous solution having the above configuration, although iodine is produced transiently, this iodine will be converted into stable iodate and/or iodite immediately. Therefore, even when air containing chlorine dioxide gas in a low concentration is kept in contact with aqueous solution of a long period, there is no risk of evaporation loss of iodine.

Further, also even in case ozone ($O_3$) present in the air is absorbed in the aqueous solution, as this ozone is decomposed by the alkaline substance contained in the aqueous solution, production of iodine through the reaction between ozone and the iodide can be prevented substantially completely for ozone which is normally present in the atmosphere in the concentration from 10 ppb to 30 ppb approximately.

For the reasons described above, when the chlorine dioxide gas entrapping agent proposed by this disclosure is employed, it is possible to entrap chlorine dioxide contained in a low concentration in air in a reliable manner, substantially without the evaporation loss of iodine or the production of iodine due to ozone.

EMBODIMENTS

Modes of Embodiment

Next, embodiments of the present disclosure will be explained.

(Chlorine Dioxide Gas Entrapping Agent)

A chlorine dioxide gas entrapping agent relating to the present disclosure comprises an aqueous solution containing an alkaline substance and an iodide.

Some examples of alkaline substance usable include lithium hydroxide, potassium hydroxide, sodium hydroxide and so on, but are not limited thereto. Further, the concentration of the alkaline substance in the aqueous solution is preferably 0.01N or more, more preferably, from 0.1N to 2N.

Some examples of iodide useable include potassium iodide, sodium iodide and so on, but are not limited thereto. Further, the concentration of the iodide in the aqueous solution is preferably 0.2 g/L or more preferably, more preferably, from 2 g/L to 50 g/L.

(Chlorine Dioxide Gas Entrapping Method)

A chlorine dioxide gas entrapping method according to this disclosure comprises a step of bringing air containing chlorine dioxide gas into contact with the above-described chlorine dioxide gas entrapping agent containing an alkaline substance and iodide.

As an example of a method for contacting, there can be cited a method of suctioning air with using a known air pump and feeding the suctioned air to the chlorine dioxide gas entrapping agent for bubbling. For instance, in case the chlorine dioxide gas concentration is determined by the iodometric titration method, for an indoor space having a volume of 50 $m^3$ or more, the suctioning/bubbling can be effected at a suctioning rate of 0.1 L/min. to 1.0 L/min. for a period of from 2 hours to 200 hours.

The chlorine dioxide gas entrapping method according to this disclosure can make determination for air which contains chlorine dioxide gas in a very low concentration of from 0.0002 ppm to 5 ppm. Needless to say, this method can be used also for air containing chlorine dioxide gas in higher concentrations.

(Chlorine Dioxide Gas Concentration Determining Method)

(1) Ion Chromatography Method

Chlorine dioxide gas entrapped with using the above-described chlorine dioxide gas entrapping agent and the above-described chlorine dioxide gas entrapping method is present in the form of very stable iodate ions and/or iodite ions in the chlorine dioxide gas entrapping agent which comprises an alkaline aqueous solution. Therefore, through direct determination of concentrations of these ions by the known ion chromatography method, a concentration of chlorine dioxide gas in air can be determined. Incidentally, since the ion chromatography method has higher detection sensitivity than the iodometric titration method, determination is possible even for an amount of suctioned air which is about only about 1/10 of that of the case using the iodometric titration method.

(2) Colorimetric Method

Chlorine dioxide gas entrapped with using the above-described chlorine dioxide gas entrapping agent and the above-described chlorine dioxide gas entrapping method is present in the form of very stable iodate ions and/or iodite ions in the chlorine dioxide gas entrapping agent which comprises an alkaline aqueous solution.

When e.g. sulfuric acid from 1N to 18N is added to this chlorine dioxide gas entrapping agent to render this acidic, immediate release of iodine occurs, as shown by the Chemical Formulae (7) and (8) above.

Therefore, it becomes possible to determine iodine concentration by the known colorimetric method using a coloring reagent such as an aqueous starch solution, a DPD reagent and a colorimeter. With this, a concentration of chlorine dioxide gas contained in a low concentration in air can be determined even more easily. Incidentally, since the colorimetric method has higher detection sensitivity than the iodometric titration method, determination is possible even for an amount of suctioned air which is about only about 1/2 of that of the case using the iodometric titration method.

(3) Iodometric Titration Method

Chlorine dioxide gas entrapped with using the above-described chlorine dioxide gas entrapping agent and the above-described chlorine dioxide gas entrapping method is present in the form of very stable iodate ions and/or iodite ions in the chlorine dioxide gas entrapping agent which comprises an alkaline aqueous solution.

When e.g. sulfuric acid from 1N to 18N is added to this chlorine dioxide gas entrapping agent to render this acidic, immediate release of iodine occurs, as shown by the Chemical Formulae (7) and (8) above.

Therefore, it becomes possible to determine iodine concentration by the known iodometric titration method effecting titration with sodium thiosulfate reference liquid ("hypo liquid"). With this, a concentration of chlorine dioxide gas contained in a low concentration in air can be determined even more easily.

EXAMPLES

Next, the present disclosure will be explained in greater details by way of Examples thereof. It is understood, however that the present disclosure is not limited to these examples.

Example 1

By a continuous operation with using an electrolysis type chlorine dioxide generating machine ("LISPASS S", manufactured by Taiko Pharmaceutical Co., Ltd.), chlorine dioxide gas was generated at a gas flow rate: 300 mL/min and in a generation rate: 5 mg/hr.

A portion of the generated gas was drawn by a corrosion resistant air pump at a rate of 50 mL/min and then diluted with diluting air of 3 L/min. Further, this diluted air was drawn at the rate of 50 mL/min by the corrosion resistant air pump and diluted then with diluting air at a rate of 2.5 L/min, whereby air containing chlorine dioxide in a concentration of 30 ppb approximately was generated continuously.

As chlorine dioxide gas entrapping agents, there were prepared aqueous solutions containing potassium iodide: 50 g/L and potassium hydroxide: 50 g/L, respectively. And, 20 mL of these were introduced respectively into 30 mL impingers.

The two columns of introduced impingers are connected in series and the above-described chlorine dioxide gas was suctioned at a rate of 500 mL/min for 30 hours.

The entrapping agents inside the first and second columns of impingers were put into flasks respectively and then 2 N sulfuric acid was added thereto to render them acidic, and titration was effected with 0.01 mol/L of sodium thiosulfate reference liquid. The titration numbers were 0.55 mL for the first column and 0.00 mL for the second column. The factor of the sodium thiosulfate reference liquid was 1.005 and calculations made showed 29.6 ppb for the first column (incidentally, the theoretical value was 31.9 ppb) and 0 ppb for the second column.

Example 2

The chlorine dioxide gas generated from the chlorine dioxide gas generating device used in Example 1 (flow rate: 2.55 L/min, concentration: about 30 ppb) was mixed with air at 2.5 L/min having an ozone concentration: 50 ppb generated from an ozone generator (Model 1410, manufactured by Dylec Inc., an air purifier Model 1400, Monitor Model 1150) and determination was effected similarly to Example 1.

The chlorine dioxide gas concentration and the ozone concentration of the feed gas were calculated to produce the results: chlorine dioxide gas: $2.55/(2.55+2.5) \times 29.6 = 14.9$ ppb, and ozone: $2.5/(2.55+2.5) \times 50 = 24.8$ ppb.

The titration numbers were found as: 0.30 mL for the first column and 0.00 mL for the second column. The factor of the sodium thiosulfate reference liquid was 1.005 and calculations made showed 16.1 ppb for the first column and 0 ppb for the second column.

Example 3

Like Example 1 above, air containing chlorine dioxide gas in a concentration of 30 ppb approximately was generated continuously. As absorption liquids, there were prepared aqueous solutions containing potassium iodide: 10 g/L and potassium hydroxide: 2 g/L, respectively. And, 20 mL of these were introduced respectively into 30 mL impingers.

The two columns of introduced impingers are connected in series and the above-described chlorine dioxide gas was suctioned at a rate of 500 mL/min for 30 hours. The absorption liquids inside the first and second columns of impingers were put into flasks respectively and then 2 N sulfuric acid was added thereto to render them acidic, and titration was effected with 0.01 mol/L of sodium thiosulfate reference liquid.

The titration numbers were found as: 0.53 mL for the first column and 0.00 mL for the second column. The factor of the sodium thiosulfate reference liquid was 1.005 and calculations made showed 28.5 ppb for the first column and 0 ppb for the second column.

Example 4

Like Example 2 above, air with ozone concentration of 50 ppb was mixed at a rate of 2.5 L/min and determination was made similarly to Example 2.

The feed gas had concentrations of: chlorine dioxide: 14.9 ppb and ozone: 24.8 ppb. As absorption liquids, there were prepared aqueous solutions containing potassium iodide: 10 g/L and potassium hydroxide: 2 g/L, respectively. And, 20 mL of these were introduced respectively into 30 mL impingers.

The two columns of introduced impingers are connected in series and the above-described chlorine dioxide gas was suctioned at a rate of 500 mL/min for 30 hours. The absorption liquids inside the first and second columns of impingers were put into flasks respectively and then 2 N sulfuric acid was added thereto to render them acidic, and titration was effected with 0.01 mol/L of sodium thiosulfate reference liquid.

The titration numbers were found as: 0.28 mL for the first column and 0.00 mL for the second column. The factor of the reference liquid was 1.005 and calculations made showed 14.1 ppb for the first column and 0 ppb for the second column.

Comparison Example 1 (Conventional Method)

Like Example 1 above, air containing chlorine dioxide gas in a concentration of 30 ppb approximately was generated continuously. As absorption liquids, there was prepared aqueous solution containing potassium iodide: 10 g/L, respectively. And, 20 mL of this was introduced respectively into 30 mL impingers.

The two columns of introduced impingers are connected in series and the above-described chlorine dioxide gas was suctioned at a rate of 500 mL/min for 30 hours. The absorption liquids inside the first and second columns of impingers were put into flasks respectively and then 2 N sulfuric acid was added thereto to render them acidic, and titration was effected with 0.01 mol/L of sodium thiosulfate reference liquid.

The titration numbers were found as: 0.42 mL for the first column and 0.07 mL for the second column. The factor of the reference liquid was 1.005 and calculations made showed 22.6 ppb for the first column and 3.8 ppb for the second column. Thus, in comparison with Example 3, the absorption entrapment of chlorine dioxide gas was insufficient and there was a significant minus error in the determined value for the first column.

Comparison Example 2 (Conventional Method, Under Neutral Condition)

Like Example 1 above, air containing chlorine dioxide gas in a concentration of 30 ppb approximately was generated continuously. As absorption liquid, to an aqueous solution of potassium iodide: 10 g/L, potassium dihydrogen phosphate and dipotassium hydrogen phosphate buffer solution were added to adjust pH to 7 to 8 and to 30 mL impingers prepared, 20 mL of the above absorption liquid was introduced.

The two columns of introduced impingers are connected in series and the above-described chlorine dioxide gas was suctioned at a rate of 500 mL/min for 30 hours. The absorption liquids inside the first and second columns of impingers were put into flasks respectively and then 2 N sulfuric acid was added thereto to render them acidic, and titration was effected with 0.01 mol/L of sodium thiosulfate reference liquid.

The titration numbers were found as: 0.43 mL for the first column and 0.06 mL for the second column. The factor of the reference liquid was 1.005 and calculations made showed 23.1 ppb for the first column and 3.2 ppb for the second column. Thus, in comparison with Example 3, the absorption entrapment of chlorine dioxide gas was insufficient and there was a significant minus error in the determined value for the first column.

Comparison Example 3 (Conventional Method)

By the method similar to Example 2, gas containing chlorine dioxide: 14.9 ppb and ozone: 24.8 ppb was fed and as absorption liquid there was prepared aqueous solution containing potassium iodide: 10 g/L and to 30 mL impingers prepared, 20 mL of the respective absorption liquid was introduced.

The titration numbers were found as: 0.34 mL for the first column and 0.04 mL for the second column. The factor of the reference liquid was 1.005 and calculations made showed 18.3 ppb for the first column and 2.2 ppb for the second column. Thus, in comparison with Example 4, there was a significant plus error in the determined value for the first column, due to influence from ozone.

INDUSTRIAL APPLICABILITY

The present disclosure allows accurate determination of a concentration of chlorine dioxide gas contained in a low concentration in air. So, this disclosure can be used advantageously for evaluation or performance confirmation of e.g.

deodorant agent releasing chlorine dioxide gas into a room for decomposing odorous component or a medical agent for removing/killing virus or bacteria afloat in a room or for calibration of an instrument for continuously determining a concentration of chlorine dioxide gas with high sensitivity.

The invention claimed is:

1. A chlorine dioxide gas entrapping method comprising the steps of using an alkaline aqueous solution containing a strong alkaline substance and an iodide and bringing air containing the chlorine dioxide gas into contact with the aqueous solution, and reacting the strong alkaline substance, the iodide, and the chlorine dioxide gas to produce iodate and/or iodite, chloride, and water, wherein the strong alkaline substance contained in the aqueous solution has a concentration of 0.01 N or more.

2. The chlorine dioxide gas entrapping method according to claim 1, wherein the chlorine dioxide gas contained in the air is present in a concentration ranging from 0.0002 ppm to 5 ppm.

3. The chlorine dioxide gas entrapping method according to claim 1, wherein the iodide contained in the aqueous solution has a concentration of 0.2 g/L or more.

4. A chlorine dioxide gas concentration determining method, the method implementing the chlorine dioxide gas entrapping method according to claim 1, wherein the determining method comprises a step of determining, with using an ion chromatography technique, the concentration of iodate and/or iodite in the aqueous solution contacted with the air containing the chlorine dioxide gas.

5. A chlorine dioxide gas concentration determining method, the method implementing the chlorine dioxide gas entrapping method according to claim 1, wherein the determining method comprises the steps of making acidic the aqueous solution contacted with the air containing the chlorine dioxide gas so as to release iodine and determining the concentration of the iodine by colorimetric method or iodometric titration method.

6. A chlorine dioxide gas entrapping agent used in the chlorine dioxide gas entrapping method according to claim 1, the agent comprising an aqueous solution containing a strong alkaline substance and an iodide.

7. The chlorine dioxide gas entrapping method according to claim 1, wherein the strong alkaline substance is a hydroxide of alkali metal.

8. The chlorine dioxide gas entrapping method according to claim 7, wherein the hydroxide of alkali metal is selected from a group consisting of lithium hydroxide, potassium hydroxide and sodium hydroxide.

9. The chlorine dioxide gas entrapping agent according to claim 6, wherein the strong alkaline substance is a hydroxide of alkali metal.

10. The chlorine dioxide gas entrapping agent according to claim 9, wherein the hydroxide of alkali metal is selected from a group consisting of lithium hydroxide, potassium hydroxide and sodium hydroxide.

* * * * *